(12) United States Patent
Liu et al.

(10) Patent No.: US 9,227,931 B1
(45) Date of Patent: Jan. 5, 2016

(54) BIFUNCTIONAL COMPOUND AND METHOD FOR MANUFACTURING THE SAME

(71) Applicant: ATOMIC ENERGY COUNCIL-INSTITUTE OF NUCLEAR ENERGY RESEARCH, Taoyuan County (TW)

(72) Inventors: Show-Wen Liu, Taoyuan County (TW); Yu Chang, Taoyuan County (TW); Cheng-Fang Hsu, Taoyuan County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 0 days.

(21) Appl. No.: 14/445,183

(22) Filed: Jul. 29, 2014

(51) Int. Cl.
*C07C 323/41* (2006.01)
*C07C 319/18* (2006.01)
*C07C 319/20* (2006.01)

(52) U.S. Cl.
CPC ............. *C07C 323/41* (2013.01); *C07C 319/18* (2013.01); *C07C 319/20* (2013.01)

(58) Field of Classification Search
None
See application file for complete search history.

(56) References Cited

PUBLICATIONS

Huang et al. (Bioconjugate Chem., 2006, 17(6), 1592).*

* cited by examiner

*Primary Examiner* — Rosalynd Keys
*Assistant Examiner* — Jennifer C Sawyer
(74) *Attorney, Agent, or Firm* — Rosenberg, Klein & Lee

(57) ABSTRACT

A bifunctional compound and a method for manufacturing the same are revealed. The structural formula of the compound includes two main functional groups. One functional group is a diamide dithiolate ($N_2S_2$) ligand able to bind with radioisotopes. The other functional group is polybasic carboxylic acid that binds to biochemical substances. Based on properties of the above two functional groups, the compound of the present invention can be used for preparation of radiopharmaceuticals such as radiotracter for disease diagnosis or radioactive therapeutic agent for disease treatment.

9 Claims, No Drawings

BIFUNCTIONAL COMPOUND AND METHOD FOR MANUFACTURING THE SAME

FIELD OF THE INVENTION

The present invention relates to a compound and a method for manufacturing the same, especially to a bifunctional compound-6-{3,6-diaza-5-oxo-3-[2-((triphenylmethyl)thio)ethyl]-8-[(triphenylmethyl)thio]}-octamido-2-$N_\alpha$,$N_\alpha$-diacetic-hexyltriacid dihydrochloride that includes two types of functional groups able to bind to radioisotopes and biochemical substances respectively and a method for manufacturing the same. Thus the bifunctional compound can be applied to radiotracers or radioactive therapeutic agents.

BACKGROUND OF THE INVENTION

Receptors are found inside or on surface of human cells. Specific substances including alcohols, carbohydrates, amines, amino acids, peptides or proteins can bind to the receptors for communication between the cell and the outside world. Based on such property, the specific substances are connected to radioactive elements first. Then the radio-labeled compounds enter human bodies through the receptors and retain at specific organs or tissues. Thus the purposes of diagnostic imaging or disease treatment in the radiopharmaceutical field can be achieved.

The structural formula of the compound includes two different types of functional groups. One end of the compound is a functional group that forms a covalent bonding such as amide, thiourea, ester, alkylated amine, etc. The other end of the compound includes an electron provider such as nitrogen, oxygen, or sulfur able to transfer electrons to metals so as to form stable metal complexes. The bifunctional compound means the compound able to bind to specific substances and radioisotopes at the same time.

$^{99m}$Tc is present in more than 85% of currently available radiopharmaceuticals for diagnostic imaging. The design of Tc-99m radiopharmaceuticals is based on coordination chemistry of Technetium (Tc). Technetium forms various types of oxides with oxygen and technetium (V) oxide is the most stable. Technetium can easily form chemical bonds with atoms having lone pair of electrons such as nitrogen, sulfur, oxygen, etc in a ligand to form stable complexes with pyramidal geometry.

As to bonding of biochemical substances, the compound containing polybasic carboxylic acids is used for bonding to at least two substances. The bonding force between polybasic substances and the receptor is far more larger than the bonding force between a single substance and the receptor. For example, the affinity of a substance with three N-acetylgalactosamine (GalNAc) to asialo-glycoprotein receptor (AS-GPR) on surface of liver cells is 106 times of the affinity of a substance with a single GalNAc. In order to increase the affinity between the substance and the receptor, the compound able to bind to polybasic substances can be used.

SUMMARY

Therefore it is a primary object of the present invention to provide a bifunctional compound whose structural formula includes a $N_2S_2$ ligand able to bind to radioisotopes and three active carboxylic acid ester groups. The $N_2S_2$ ligand consists of a tertiary amine, an amide and two thiol groups. The active carboxylic acid ester groups react with amino groups of compounds to form amides so that the bifunctional compound can bind to biochemical substances. Due to these two types of functional groups, the bifunctional compound of the present invention has more functions and applications. The bifunctional compound can be used for preparing radiopharmaceuticals such as radiotracers for diagnosis or radioactive therapeutic agent for treatment.

It is another object of the present invention to provide a method for manufacturing a bifunctional compound. The bifunctional compound with two kinds of functional groups—a ligand and polybasic carboxylic acid is prepared by a series of chemical reactions. Based on properties of these functional groups, the compound can be applied to imaging or radioactive treatment after being bonded to radioisotopes and tissues/organs of living bodies.

In order to achieve the above objects, a bifunctional compound and a method for manufacturing the same according to the present invention are provided. The bifunctional compound is represented by the following structural formula:

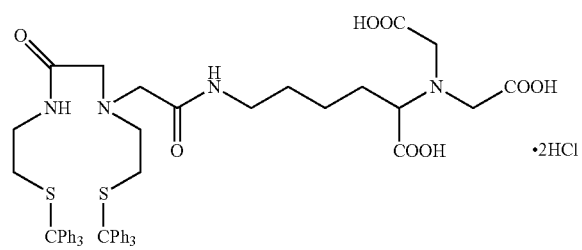

DETAILED DESCRIPTION

Please refer to following embodiments for details, features and effects of the present invention.

A compound revealed in the present invention is 6-{3,6-diaza-5-oxo-3-[2-((triphenylmethyl)thio)ethyl]-8-[(triphenylmethyl)thiol]}-octamido-2-$N_\alpha$,$N_\alpha$-diacetic-hexyltriacid dihydrochloride that includes two kinds of functional groups—diamide dithiolate ligand and polybasic carboxylic acid. The diamide dithiolate ligand is a chelating agent. By these two types of functional groups, the compound has more functions and wider applications.

The polybasic carboxylic acid (a plurality of carboxylic acid groups) is used to bind to biochemical substances such as compounds with hydroxyl groups (alcohols and carbohydrates) or compounds having amino groups (amines, amino acids, peptides and proteins). As to the diamide dithiolate ($N_2S_2$) ligand, it is formed by a tertiary amine, an amide and two thiol groups and is able to bind to radioisotopes Rhenium (Re)-186, Re-186, Technetium (Tc)-95m, Tc-99 or Tc-99m to form neutral complexes. Based on properties of the two types of functional groups, the compound of the present invention can be used to prepare diagnostic radiotracers for organs or tissues and radioactive therapeutic agents with target specificity.

Moreover, the thiol group in the N2S2 ligand is protected by triphenylmethyl group so that the compound has stable chemical properties which result in convenience in storage. Thiols are easily oxidized in neutral or alkaline solution. The oxidized thiol group is unable to react with radioisotopes. Thus the thiols need to be protected in advance. In order to activate the compound in storage, the compound is dissolved in trifluoroacetic acid and then overdose triethylsilane is added into the solution. Thus triphenylmethyl group is released from thiol group to form solid that is insoluble in trifluoroacetic acid. Then the solid can be removed by filtration or wash with n-hexane. These methods are simple and convenient. Furthermore, the bond energy between triphenylmethyl group and sulfur atom is lower. When heavy metals are present, the bond therebetween (S—CPh$_3$) is easy to break and a bond between heavy metals and sulfur atom is formed. Thus the triphenylmethyl group for protection is automatically released during complex reaction between thiol group and radioisotopes. There is no need to remove the protection group in advance.

In a method for manufacturing a bifunctional compound according to the present invention, 2-thioethylamine hydrochloride is used as initial reactant. Refer to chemical equation 1, 2-thioethylamine hydrochloride reacts with triphenylmethanol under catalysis of borontrifluoride ethyl ether complex. The sulfur in 2-thioethylamine hydrochloride is bonded to triphenylmethyl group of triphenylmethanol for protection of thiol group and 2-[(triphenylmethyl)thio]ethylamine (hereafter referred to as compound 1) is obtained.

(equation 1)

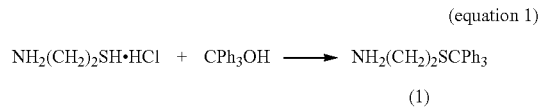

(1)

Refer to chemical equation 2, take compound 1 and chloroacetyl chloride to carry out amidation and get N-[2-((triphenylmethyl)thio)ethyl]chloroacetamide (hereafter referred to as compound 2).

(equation 2)

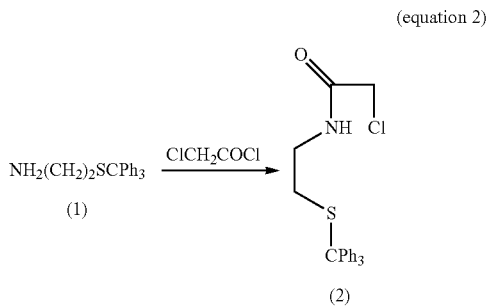

Refer to chemical equation 3, use compound 1 and compound 2 obtained in the previous reaction to perform a substitution reaction and produce N-[2-((triphenylmethyl)thio)ethyl][2-((triphenylmethyl)thio)ethylamino]acetamide (hereafter referred to as compound 3). The compound 3 contains an amine-amide-thiol ligand.

(equation 3)

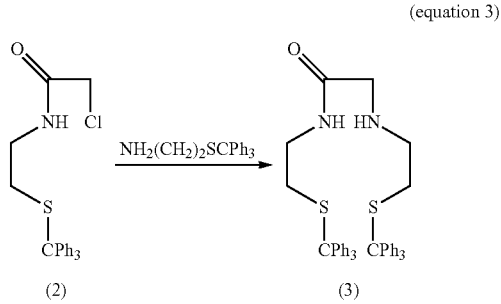

Next refer to chemical equation 4, use compound 3 and methyl bromoacetate to carry out substitution reaction in alkaline acetonitrile solution and get methyl-3,6-diaza-5-oxo-3-[2-((triphenylmethyl)thio)ethyl]-8-[(triphenylmethyl)thio]octanoate (hereafter referred to as compound 4).

(equation 4)

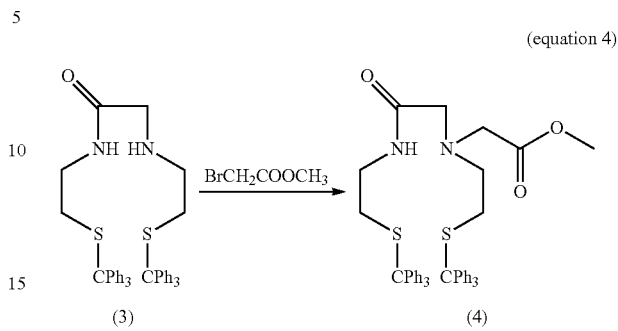

Refer to chemical equation 5, hydrolyze compound 4 in alkaline methanol solution and then neutralize the solution to get 3,6-diaza-5-oxo-3-[2-((triphenylmethyl)thio)-ethyl]-8-[(triphenylmethyl)thio]octanoic acid (hereafter called compound 5).

(equation 5)

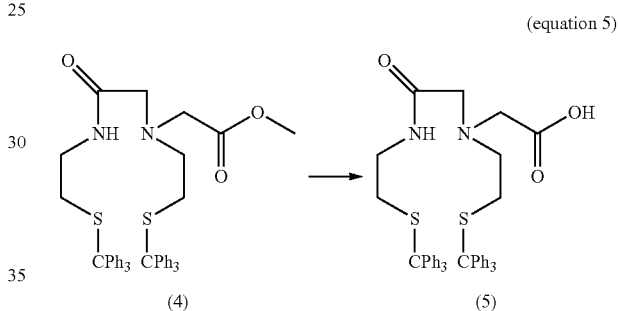

Take N$_\alpha$,N$_\alpha$Bis(carboxymethyl)-L-lysine hydrate and 1.25M hydrochloric acid dissolved in methanol solution to perform esterification and get N$_\alpha$,N$_\alpha$-Bis(methoxycarbonylmethyl)-L-lysinate methyl ester (hereafter called compound 6), as shown in chemical equation 6.

(equation 6)

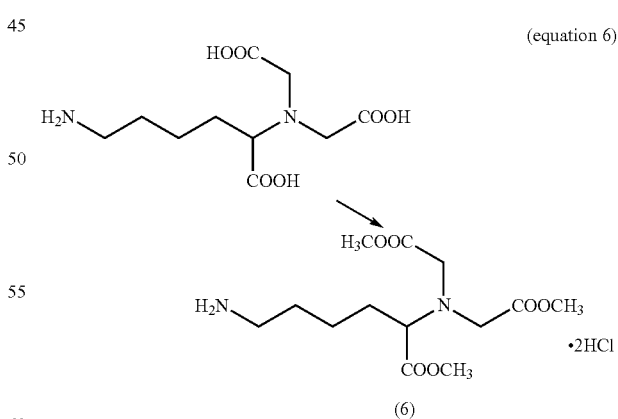

As shown in chemical equation 7, use compound 5 with activated carboxylic acid and compound 6 to carry out amidation and get 5-N$_\alpha$,N$_\alpha$-Bis(methoxy carbonylmethyl)-methoxycarbonylpentyl 3,6-diaza-5-oxo-3-[2-((triphenylmethyl)thio)ethyl]-8-[(triphenylmethyl)thio]}octamide (hereafter compound 7).

(equation 7)

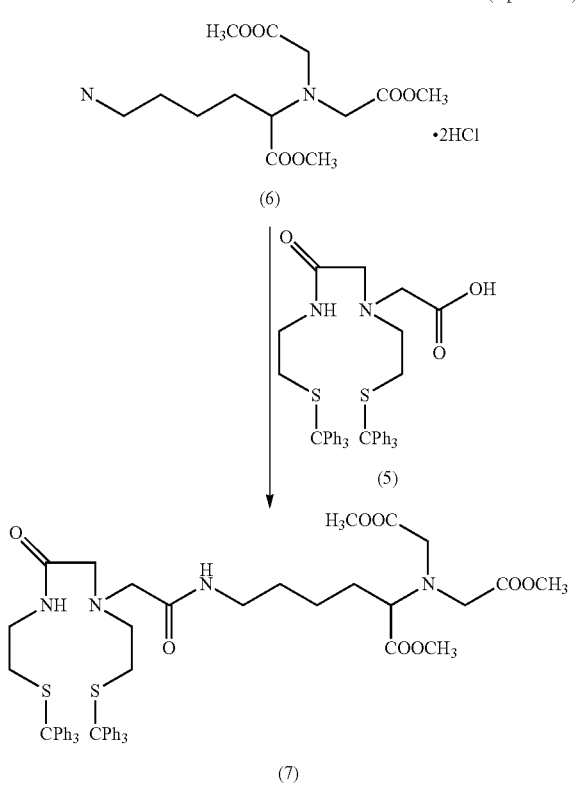

Refer to chemical equation 8, hydrolyze compound 7 to get final product 6-{3,6-diaza-5-oxo-3-[2-((triphenylmethyl)thio)ethyl]-8-[(triphenylmethyl)thio]}-octamido-2-$N_\alpha$,$N_\alpha$-diacetic-hexyltriacid dihydrochloride, abbreviated as OCTAMTA.2HCl. OCTAM is captured from octamido, representing the structure of $N_2S_2$. TA.2HCl means triacid dihydrochloride that contains the structure of three carboxylic acid groups. The abbreviation reflects the structure features of bifunctional compound of the present invention.

(equation 8)

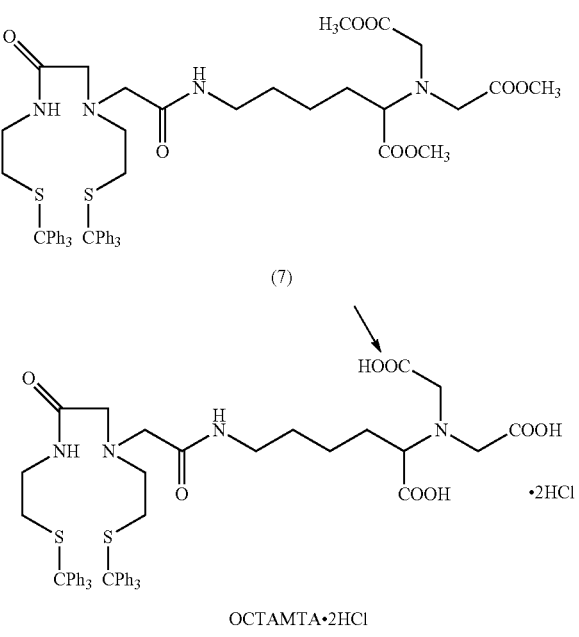

The yield rate of the final product OCTAMTA.2HCl obtained according to the above eight steps is 8.38% and its structure is confirmed by infrared spectroscopy analysis and nuclear magnetic resonance spectroscopy analysis. Thus the method for manufacturing OCTAMTA.2HCl of the present invention is feasible.

The followings are data controlled during operation of the present invention and related details.

Synthesis of compound 1: Take and dissolve 5 g (44.2 mmol) 2-thioethylamine hydrochloride, 11 g (42.5 mmol) triphenylmethanol and 7 mL (49.9 mmol) triethylamine in 80 mL trichloromethane (chloroform). After the solution being heated at 75° C. and refluxed, slowly drop 15 mL (120 mmol) boron trifluoride ethyl ether complex used as catalyst into the solution. The mixed solution is continuously heated to reflux for 4 hours. After vacuum evaporation, dissolve residue with methanol and concentrate the solution again. Add sodium bicarbonate aqueous solution and stir the mixture to get white solid precipitate. After vacuum filtration, take the solid. Wash the solid with water and then dry to get 14 g (99%) solid product (compound 1).

Analysis of compound 1:IR (neat) 3381 ($NH_2$) $cm^{-1}$. $^1H$ NMR ($CDCl_3$) 7.42 (m, 3 H, Ph), 7.30 (m, 12 H, Ph), 2.58 (t, J=6.6 Hz, 2 H, $CH_2N$), 2.32 (t, J=6.6 Hz, 2 H, $CH_2S$), 1.45 (br, 2 H, NH). $^{13}C$ NMR ($CDCl_3$) 144.80, 192.52, 127.81 & 126.60 (Ph), 66.51 (CPh), 40.94 ($CH_2N$), 36.09 ($CH_2S$). MS m/z 319 ($M^+$), 243 ($M^+$-$C_6H_5^{+1}$).

Synthesis of compound 2: Dissolve 5.24 g (16.4 mmol) compound 1 and 2.76 mL (19.6 mmol) triethylamine in 100 mL trichloromethane. Being cooled down in an ice bath, slowly drop 1.56 mL (19.6 mmol) chloroacetyl chloride dissolved in 20 mL trichloromethane solution. Then stir the mixture at room temperature for 2 hours. Wash organic phase with follows in turn: 1N hydrogen chloride solution (150 mL), saturated sodium carbonate solution (150 mL) and water (150 mL). The organic phase is dried by anhydrous sodium sulfate and then vacuum evaporated to get 5.62 g (86.6%) yellow oily product, compound 2.

Analysis of compound 2:IR (neat) 3413 & 3306 (NH), 1662 (CO) $cm^{-1}$. $^1H$ NMR ($CDCl_3$) 7.41 (m, 3 H, Ph), 7.24 (m, 12 H, Ph), 6.48 (br, 1 H, NH), 3.97 (s, 2 H, $CH_2Cl$), 3.12 (q, J=6.3 Hz, 2 H, $CH_2N$), 2.43 (t, J=6.3 Hz, 2 H, $CH_2S$). $^{13}C$ NMR ($CDCl_3$) 165.63 (CO), 144.47, 129.48, 127.97 & 126.81 (Ph), 66.52 (CPh), 42.54 ($CH_2Cl$), 38.35 ($CH_2N$), 31.67 ($CH_2S$). MS m/z 397 & 395 ($M^+$), 243 (($CPh_3$)$^+$).

Synthesis of compound 3: Dissolve 5.4 g (13.8 mmol) compound 2 and 4.4 g (13.8 mmol) compound 1 in 100 mL dichloromethane. Then add 3 mL (20.8 mmol) triethylamine into the solution. The mixture is heated to reflux at 55° C. for 2 days. Alter being cooled down, wash with sodium bicarbonate aqueous solution (120 mL) and water (120 mL×1) in turn, and take organic phase. The organic phase is dried by sodium sulfate, concentrated and then treated by liquid chromatography ($SiO_2$, ethyl acetate:n-hexane=1:1) for isolation and purification to get 2.2 g (41.8%) light yellow oily product (compound 3).

Analysis of compound 3:IR (neat) 3330 (NH), 1670 (CO) $cm^{-1}$. $^1H$ NMR ($CDCl_3$) 7.42 (m, 4 H, HNCO & Ph), 7.20 (m, 12 H, Ph), 3.07 (m, 4 H, $CH_2NCO$ & $CH_2CO$), 2.38 (m, 6 H, $CH_2NHCH_2CO$ & $CH_2S$), 1.94 (br, 1 H, $NHCH_2CO$). $^{13}C$ NMR ($CDCl_3$) 170.84 (CO), 144.61, 129.47, 127.88 & 126.69 (Ph), 66.72 & 66.65 (CPh3), 51.62 ($CH_2CO$), 48.19 ($CH_2NHCH_2CO$), 37.70 ($CH_2NHCO$), 32.12 & 31.97 ($CH_2S$). MS m/z 243 (($CPH_3$)$^+$).

Synthesis of compound 4: Take 0.73 mL (7.73 mmol) methyl bromoacetate, 2.1 g (3.1 mmol) compound 3, 0.65 mL (4.65 mmol) triethylamine and 50 mL acetonitrile to be heated and refluxed at 85° C. overnight. The preferred reaction time is 24 hours. After being cooled down and vacuum evaporated, the residue is dissolved in 100 mL dichloromethane and washed with 100 mL water. Remove the aqueous phase, take the organic phase to be dried with sodium sulfate ($Na_2SO_4$) and concentrated. Then use liquid chromatography ($SiO_2$, ethyl acetate:n-hexane=1:1) for isolation and purification to get 1.25 g (53.7%) pale yellow oily product (compound 4).

Analysis of compound 4:IR (neat) 3349 (NH), 1743 & 1675 (CO) $cm^{-1}$. $^1H$ NMR ($CDCl_3$) 7.55 (NH), 7.40 (m, 3 H, Ph), 7.22 (m, 12 H, Ph), 3.61 (s, 3 H, $CH_3$), 3.20 (s, 2 H, $CH_2CO$), 3.06 (m, 4 H, $CH_2CO$ & C$\underline{H}_2$NH), 2.56 (t, J=6.6 Hz, 2 H, $CH_2N$), 2.39 (t, J=6.6 Hz, $CH_2S$), 2.28 (t, J=6.6 Hz, $CH_2S$).$^{13}C$ NMR ($CDCl_3$) 170.89 & 170.21 (CO), 144.68, 144.57, 129.51, 129.47, 127.89, 127.86, 126.70 & 126.62 (Ph), 66.82 & 66.63 ($CPh_3$), 58.14, 54.62 & 53.72 ($CH_2$), 51.64 ($CH_3O$), 38.0 (CH2NH), 31.90 & 29.99 ($CH_2S$). MS m/z 507 ($M^+$-$CPh_3$), 448 ($M^+$-$CPh_3$—$COOCH_3$).

Synthesis of compound 5: Use 3 g potassium hydroxide (or sodium methoxide) as a catalyst and dissolve potassium hydroxide (or sodium methoxide) in 30 mL anhydrous methanol. Add 1.0 g (1.33 mmol) compound 4 into the solution and stir the solution at room temperature for 5 hours. After vacuum evaporation at room temperature, add 5 mL water and 5 mL methanol to dissolve the compound 4 completely. Add concentrated hydrochloric acid for adjusting the pH value of the solution to 7. Use 30 mL dichloromethane to extract twice. Remove the aqueous phase and take the organic phase. The organic phase is added with anhydrous sodium sulfate for dehydration and is vacuum evaporated to get the pale yellow oily product 0.98 g (100%) (compound 5).

Analysis of compound 5:IR (neat) 3327 (NH), 1726 & 1634 (CO) $cm^{-1}$. $^1H$ NMR ($CD_3OD$) 7.40 (m, 3 H, Ph), 7.25 (m, 12 H, Ph), 3.21 (s, 2 H, $CH_2$), 3.11 (s, 2 H, $CH_2$), 2.30 (t, J=6.6 Hz, 2 H, C$\underline{H}_2$NH), 2.52 (t, J=6.6 Hz, 2 H, $CH_2N$), 2.34 (t, J=6.6 Hz, 4, $\overline{H}$, $CH_2S$). $^{13}C$ NMR ($CD_3OD$) 173.89 & 172.97 (CO), 146.11, 130.72, 128.96, 127.87 & 127.81 (Ph), 68.09 & 67.84 ($CPh_3$), 59.0, 55.86 & 55.13 ($CH_2$), 39.12 ($CH_2NH$), 32.70 & 31.01 ($CH_2S$). MS m/z 243 (($CPh_3$)$^+$.

Synthesis of compound 6: Add 0.93 g (3.54 mmol) $N_\alpha,N_\alpha$Bis(carboxymethyl)-L-lysine hydrate into 1.25M hydrochloric acid dissolved in 80 mL methanol solution and heat to reflux at 70° C. overnight. The preferred reaction time is 24 hours. The product-compound 6 (1.33 g, 100%) is obtained after vacuum evaporation.

Analysis of compound 6:IR (neat) 3430 ($NH_2$), 2955 (NH) & 1738 (CO) $cm^{-1}$. $^1H$ NMR ($CD_3OD$) 4.35 (d, 4 H, C$\underline{H}_2$CO), 4.27 (t, 1 H, CHCO), 3.85 (s, 3H, CHCOOC$\underline{H}_3$), 3.82 (s, 3H, $CH_2COOCH_3$), 2.97 (t, 2 H, C$\underline{H}_2NH_2$), 2.01 (q, 2 H, C$\underline{H}_2CH_2CH_2CH_2$), 1.75 (m, 2 H, $CH_2CH_2$C$\underline{H}_2$CH$_2$), 1.61 (q, 2 H, $CH_2$C$\underline{H}_2CH_2CH_2$). $^{13}C$ NMR ($CD_3OD$) 170.32 & 169.32 (CO), 67.48 (CH), 54.89 (C$\underline{H}_2CO$), 53.60 ($CH_3$), 40.31 (C$\underline{H}_2NH_2$), 28.50 (C$\underline{H}_2CH_2CH_2CH_2$), 27.90 ($CH_2CH_2$C$\underline{H}_2CH_2$), 23.97 ($CH_2$C$\underline{H}_2CH_2CH_2$).

Synthesis of compound 7: Set 0.65 g (0.89 mmol) compound 5, 0.34 g (0.89 mmol) compound 6, 0.61 mL (4.44 mmol) triethylamine, 0.28 g (1.33 mmol) 1,3-dicyclohexylcarbodiimide, 0.13 g (1.07 mmol) N-hydroxysuccinimide and 50 mL anhydrous dichloromethane into a 250 mL round-bottom flask evenly and stir the mixture at room temperature overnight. The preferred reaction time is 24 hours. Then perform vacuum filtration, get the filtrate and concentrate the filtrate. Add acetone for dissolution, concentrate the dissolved, and dissolve the concentrate in chloroform. Then wash with an aqueous solution of sodium bicarbonate several times and take the organic phase. After the organic phase being dried by sodium sulfate and concentrated, use liquid chromatography ($SiO_2$, $CHCl_3$:$CH_3OH$=95:5) for isolation and purification of the product-compound 7 (0.48 g, 53.1%).

Analysis of compound 7:IR (neat) 3326 & 2926 (NH), 1742 & 1666 (CO) $cm^{-1}$. $^1H$ NMR ($CDCl_3$) 7.42-7.33 (m, 6 H, Ph), 7.27-7.16 (m, 24 H, Ph), 6.97 & 6.88 (t, 2H, NH), 3.66 (s, 12H, $OCH_3$), 3.37 (t, 1H, CH), 3.13 (q, 2 H, NHC$\underline{H}_2$), 2.99 (s, 2H, $COCH_2$), 2.95 (s, 2H, $CH_2CO$), 2.49 (t, 2H, $NCH_2$), 2.39 (t, 2 H, $CH_2S$), 2.30 (t, 2H, CH2S), 1.75 (m, 2 H, NHC$\underline{H}_2CH_2CH_2CH_2$), 1.59 (m, 2H, $CH_2CH$), 1.40 (m, 2H, $NHCH_2$C$\underline{H}_2CH_2CH_2$), 1.26 (m, 2H, $NHCH_2CH_2$C$\underline{H}_2CH_2$). $^{13}C$ NMR ($CDCl_3$) □ 172.94, 171.71, 169.78, 144.54 & 144.48 (CO), 129.47, 129.42, 127.95, 127.91, 126.83 & 126.74 (Ph), 77.40, 77.18, 76.98 & 76.55 ($CPh_3$), 67.03 & 66.81 (N$CH_2$CO), 64.56 (CH), 58.40 ($CH_2N$), 57.89 (N$CH_2$CO), 53.95 ($NCH_2$), 52.32, 51.56 & 51.33 ($CH_3$), 38.88 ($NHCH_2$), 37.95 (NHC$\underline{H}_2CH_2CH_2CH_2$), 31.96 ($NHCH_2CH_2$C$\underline{H}_2CH_2$), 30.07 ($NHCH_2$C$\underline{H}_2CH_2CH_2$), 29.80 ($NHCH_2CH_2$C$\underline{H}_2CH_2$), 28.94 & 23.11 ($CH_2S$).

Synthesis of compound OCTAMT.2HCl: Use potassium hydroxide (or sodium methoxide) as a catalyst and dissolve potassium hydroxide (or sodium methoxide) in methanol solution. Add 0.14 g (0.14 mmol) compound 7 into the solution and stir at room temperature for 2 hours. After being vacuum evaporated at room temperature, add 10 mL water and 15 mL methanol for complete dissolution. Then use concentrated hydrochloric acid for adjusting the pH value of the solution to 7. Add 30 mL dichloromethane to extract twice. Remove the aqueous phase and take the organic phase. The organic phase is added with anhydrous sodium sulfate for dehydration and is vacuum evaporated to get the final product OCTAMTA.2HCl (0.15 g, 100%).

Analysis of compound OCTAMTA.2HCl:IR (neat) 3354 & 2924 (NH), 1676 (CO) $cm^{-1}$. $^1H$ NMR ($CD_3OD$) 7.40 (m, 6 H, Ph), 7.29 (m, 24 H, Ph), 3.76 & 3.74 (s, 2 H, $NCH_2CO$), 3.68-3.62 (m, 5 H, $CH_2N$,$NCH_2CO$ & CH), 3.19 (t, 2 H, NHC$\underline{H}_2CH_2CH_2CH_2$), 3.04 (q, 2 H, $NHCH_2$), 2.80 (t, 2 H, $NCH_2$), 2.59 & 2.36 (t, 4H, $CH_2S$), 1.80 (m, 2H, $NHCH_2CH_2CH_2$C$\underline{H}_2$), 1.49 (m, 4H, $NHCH_2$C$\underline{H}_2$C$\underline{H}_2CH_2$). $^{13}C$ NMR ($CD_3OD$) 174.42, 172.12, 164.63, 144.67 & 144.10 (CO), 129.32, 129.29, 128.44, 127.88, 127.63, 127.37, 126.87 & 126.54 (Ph), 67.40 & 66.55 (N$CH_2$CO), 64.52 (CH), 55.48 (COC$\underline{H}_2N$), 55.03 (C$\underline{H}_2CO$), 52.65 ($NCH_2$), 39.05 ($NHCH_2$), 38.34 (NHC$\underline{H}_2CH_2CH_2CH_2$), 31.11 ($NHCH_2CH_2$C$\underline{H}_2CH_2$), 29.32 (($NHCH_2$C$\underline{H}_2CH_2CH_2$), 28.13 & 22.88 ($CH_2S$).

In summary, a bifunctional compound and a method of the same according to the present invention are revealed. The compound includes a diamide dithiolate ligand able to bind to radioisotopes and polybasic carboxylic acid that binds to biochemical substances. Based on properties of the two functional groups, the compounds is used for preparation of radiopharmaceuticals. Moreover, the compound has the property of storage stability.

The compound revealed in the present invention has good performance in storage stability, attachment to radioisotopes, and retention in tissues or organs in living bodies. Therefore the bifunctional compound and the method for manufacturing the same of the present invention can be applied to the radiopharmaceutical field.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

The invention claimed is:

1. A method for manufacturing a bifunctional compound comprising the steps of:
   using 2-thioethylamine hydrochloride to react with triphenylmethanol for thiol protection and getting 2-[(triphenylmethyl)thio]ethylamine (hereafter referred to as compound 1);
   taking the compound 1 and chloroacetyl chloride to carry out amidation and get N-[2-((triphenylmethyl)thio)ethyl]chloroacetamide (hereafter referred to as compound 2);
   using the compound 1 and the compound 2 to perform a substitution reaction and produce N-[2-((triphenylmethyl)thio)ethyl][2-((triphenylmethyl)thio)ethylamino]acetamide (hereafter referred to as compound 3);
   using the compound 3 and methyl bromoacetate to carry out substitution reaction in alkaline acetonitrile solution and get methyl-3,6-diaza-5-oxo-3-[2-((triphenylmethyl)thio)ethyl]-8-[(triphenylmethyl)thio]octanoate (hereafter referred to as compound 4);
   hydrolyzing the compound 4 in alkaline methanol solution and then neutralizing the solution to get 3,6-diaza-5-oxo-3-[2-((triphenylmethyl)thio)-ethyl]-8-[(triphenylmethyl)thio]octanoic acid (hereafter called compound 5);
   taking $N_\alpha,N_\alpha$Bis(carboxymethyl)-L-lysine hydrate and hydrochloric acid dissolved in methanol solution to perform esterification and get $N_\alpha,N_\alpha$-Bis(methoxycarbonyl methyl)-L-lysinate methyl ester (hereafter called compound 6);
   using the compound 5 and the compound 6 to carry out amidation and get 5-$N_\alpha,N_\alpha$-Bis(methoxy carbonylmethyl)-methoxycarbonylpentyl 3,6-diaza-5-oxo-3-[2-((triphenylmethyl)thio)ethyl]-8-[(triphenylmethyl)thio]}octamide (hereafter compound 7); and
   hydrolyzing the compound 7 to get the bifunctional compound-6-{3,6-diaza-5-oxo-3-[2-((triphenylmethyl)thio)ethyl]-8-[(triphenylmethyl)thio]}-octamido-2-$N_\alpha$, $N_\alpha$-diacetic-hexyltriacid dihydrochloride.

2. The method as claimed in claim 1, wherein in the step of using 2-thioethylamine hydrochloride to react with triphenylmethanol for thiol protection, borontrifluoride ethyl ether complex is used as catalyst; reaction temperature is 75° C. and reaction time is 4 hours.

3. The method as claimed in claim 1, wherein in the step of taking the compound 1 and chloroacetyl chloride to carry out amidation, the amidation is performed in trichloromethane solution; reaction temperature is room temperature and reaction time is 2 hours.

4. The method as claimed in claim 1, wherein in the step of using the compound 1 and the compound 2 to perform a substitution reaction, the substitution reaction is carried out in dichloromethane, and triethylamine is used as a reactant; reaction temperature is 55° C. and reaction time is 48 hours.

5. The method as claimed in claim 1, wherein in the step of using the compound 3 and methyl bromoacetate to carry out substitution reaction in alkaline acetonitrile solution; triethylamine is used as a reactant; reaction temperature is 85° C. and reaction time is 24 hours.

6. The method as claimed in claim 1, wherein in the step of hydrolyzing the compound 4 in alkaline methanol solution, potassium hydroxide or sodium methoxide is used as a catalyst; reaction temperature is room temperature and reaction time is 5 hours.

7. The method as claimed in claim 1, wherein in the step of taking $N_\alpha,N_\alpha$Bis(carboxymethyl)-L-lysine hydrate and hydrochloric acid dissolved in methanol solution to perform esterification, reaction temperature is 70° C. and reaction time is 24 hours.

8. The method as claimed in claim 1, wherein in the step of using the compound 5 and the compound 6 to carry out amidation, 1,3-dicyclohexylcarbodiimide and N-hydroxysuccinimide are used as reactants and the amidation is carried out in dichloromethane solution; reaction temperature is room temperature and reaction time is 24 hours.

9. The method as claimed in claim 1, wherein in the step of hydrolyzing the compound 7, potassium hydroxide or sodium methoxide is used as catalyst and hydrolyzing is performed in methanol solution; reaction temperature is room temperature and reaction time is 2 hours.

* * * * *